(12) United States Patent
Gagnon-Turcotte et al.

(10) Patent No.: US 11,366,977 B2
(45) Date of Patent: Jun. 21, 2022

(54) SYSTEM AND METHOD FOR DETECTING SPIKES IN NOISY SIGNALS

(71) Applicant: UNIVERSITÉ LAVAL, Québec (CA)

(72) Inventors: Gabriel Gagnon-Turcotte, Chambly (CA); Benoit Gosselin, Lac-Beauport (CA)

(73) Assignee: UNIVERSITÉ LAVAL, Québec (CA)

( * ) Notice: Subject to any disclaimer, the term of this patent is extended or adjusted under 35 U.S.C. 154(b) by 1153 days.

(21) Appl. No.: 15/753,823

(22) PCT Filed: Aug. 23, 2016

(86) PCT No.: PCT/CA2016/050991
§ 371 (c)(1),
(2) Date: Feb. 20, 2018

(87) PCT Pub. No.: WO2017/031581
PCT Pub. Date: Mar. 2, 2017

(65) Prior Publication Data
US 2019/0012515 A1      Jan. 10, 2019

Related U.S. Application Data

(60) Provisional application No. 62/209,103, filed on Aug. 24, 2015.

(51) Int. Cl.
*G06K 9/00*       (2022.01)
*G06F 17/10*     (2006.01)
(Continued)

(52) U.S. Cl.
CPC .............. *G06K 9/0053* (2013.01); *A61B 5/24* (2021.01); *A61N 1/362* (2013.01); *G06F 3/01* (2013.01);
(Continued)

(58) Field of Classification Search
CPC ................................................... G06K 9/0053
See application file for complete search history.

(56) References Cited

U.S. PATENT DOCUMENTS

| 2010/0081958 A1 | 1/2010 | She |
| 2012/0041293 A1* | 2/2012 | Levi .......................... A61B 5/24 |
| | | 600/377 |

(Continued)

FOREIGN PATENT DOCUMENTS

WO    WO2009144655    12/2009

OTHER PUBLICATIONS

PCT International Search Report and Written Opinion from PCT Application No. PCT/CA2016/050991 entitled System and Method for Detecting Spikes in Noisy Signals (dated Nov. 15, 2016) and all references cited therein.

(Continued)

*Primary Examiner* — John E Breene
*Assistant Examiner* — Jeffrey C Morgan
(74) *Attorney, Agent, or Firm* — Hovey Williams LLP

(57) ABSTRACT

A method for determining a threshold for spike detection in a noisy signal in real-time is provided. The method includes estimating a current variability of noise in the noisy signal according to a measured instantaneous value and a window of previous instantaneous values using a sigma-delta control loop, determining the threshold based on the estimated variability of the noise; and repeating the steps to update the estimate of the variability of the noise and adjust the threshold in real-time as the noisy signal changes. A non-transitory computer-readable storage medium for executing the method on a processing unit, and a low-power digital system implementing the method are also provided.

31 Claims, 8 Drawing Sheets

(51) Int. Cl.
*A61N 1/362* (2006.01)
*A61B 5/24* (2021.01)
*G06F 3/01* (2006.01)

(52) U.S. Cl.
CPC ......... *G06F 17/10* (2013.01); *G06K 9/00503* (2013.01)

(56) References Cited

U.S. PATENT DOCUMENTS

| | | |
|---|---|---|
| 2012/0203129 A1 | 8/2012 | Rennaker, II |
| 2015/0074501 A1* | 3/2015 | Kiss ........................ G06F 17/10 714/795 |

OTHER PUBLICATIONS

Gosselin, B. et al.: "An Ultra Low-Power CMOS Automatic Action Potential Detector", IEEE Transactions on Neural Systems and Rehabilitation Engineering, vol. 17, pp. 346-353, 2009 * See p. 347, section II *; as cited in the IPRP.

"Validation of Adaptive Threshold Spike Detector for Neural Recording" (Conf Proc IEEE Eng Med Biol Soc, vol. 6, pp. 4079-4082, 2004).

"A low-power integrated circuit for adaptive detection of action potentials in noisy signals" (Conf Proc IEEE Eng Med Biol Soc, vol. 4, pp. 3325-3328, 2004).

Gosselin, B. et al.: "An Ultra Low-Power CMOS Automatic Action Potential Detector", IEEE Transactions on Neural Systems and Rehabilitation Engineering, vol. 17, pp. 346-353, 2009. * See p. 347, section II.*.

PCT International Search Report and Written Opinion from PCT Application No. PCT/CA2016/050991 entitled System and Method for Detecting Spikes in Noisy Signals (dated Nov. 15, 2016).

* cited by examiner

Table I: Comparison of spike detector approaches using synthetic neural signal

| Signal | | SDCLT (Resources Optimized) | | | SDCLT | | | RMS | | | Wave Clus (MAD) | | |
|---|---|---|---|---|---|---|---|---|---|---|---|---|---|
| SNR | Spikes | Detected | True | False | Detected | True | False | Detected | True | False | Detected | True | False |
| 0 | 1304 | 865 | 817 | 48 | 832 | 829 | 3 | 768 | 767 | 1 | 881 | 874 | 7 |
| 5 | 1303 | 1184 | 1149 | 35 | 1240 | 1235 | 5 | 1183 | 1173 | 10 | 1276 | 1265 | 11 |
| 10 | 1306 | 1328 | 1304 | 24 | 1311 | 1306 | 5 | 1316 | 1306 | 10 | 1313 | 1306 | 7 |
| 15 | 1306 | 1312 | 1306 | 6 | 1311 | 1306 | 5 | 1311 | 1306 | 5 | 1312 | 1305 | 7 |

FIG. 8

Table II: Comparison of the MCU execution time for several methods including one chnnel at 8 MHZ

| Method | Time |
|---|---|
| SDCLT (Ressources Optimized) | 11 µs |
| SDCLT (No optimization) | 440 µs |
| RMS (Ressources Optimized) | 20 µs |

FIG. 9

Table III: Comparison of the adaptive thresholding algorithm: resource utilization versus RMS and MAD

| Method | Memory | Mults/Divs | Adds/Subs | Comps | Bit shifting | Other |
|---|---|---|---|---|---|---|
| SDCLT | 256 bits (32 bytes) | 0 0 | 2 1 | 1 > 1 == | 2 right 11 left | - |
| RMS | 2048 bytes | 2 0 | 1 1 | 0 | 2 right 8 left | 1 sqrt |
| MAD1 (Not practical) | Entire signal | 0 1 | 0 0 | Many, signal length dependent | 2 right | - |
| MAD2 | 2048 bytes | 1 0 | 0 0 | 4272 >= using QuickSort | 2 right | - |

FIG. 10

SYSTEM AND METHOD FOR DETECTING SPIKES IN NOISY SIGNALS

RELATED APPLICATIONS

This is a national stage application under 35 U.S.C. § 371 of International Patent Application No. PCT/CA2016/050991, filed Aug. 23, 2016, which claims the benefit of U.S. Provisional Application No. 62/209,103, filed Aug. 23, 2016 both of which are incorporated by reference in their entireties.

TECHNICAL FIELD

The present disclosure relates to signal processing. More particularly, it relates to systems and methods for detecting spikes in noisy signals which can be used to detect action potential in electrophysiological signals.

BACKGROUND

Electrophysiology generally involves using electrodes to measure electric signals generated by biological cells and tissues. Processing and analyzing the signals allows for meaningful data to be extracted which can be used in a number of applications. For example, when analyzing neurological signals, pulses or spikes can correspond to action potential. Being able to reliably identify action potential in such signals can be very useful for constructing a brain machine interface (BMI).

Many techniques already exist for processing electrophysiological signals. Such techniques can involve, for example, processing the signal "off-line" using computationally complex algorithms. While such techniques can provide accurate results, they are not desirable or practical in many applications. In the provided example of a BMI, it is desirable to have the signal processed "on-line" so that action potential can be identified with minimal latency, allowing for a real-time interaction between brain and machine.

Spike detection is a signal processing technique that can enable significant data rate reduction and resource savings. This is particularly useful in devices such as wireless BMIs, such as those used to study small freely moving animals. These types of BMIs are generally designed using commercial off-the-shelf (COTS) components, such as low-power general purpose transceivers which limit the maximum output data rate. On-the-fly spike detection can be employed in such systems to provide high data reduction factors by extracting the relevant portion of the signal, and by sending only the detected spikes.

Disadvantageously, these types of systems rely on low-power and resources constrained microcontrollers units (MCU) that cannot run complex signal processing tasks, such as compression and effective spike detection. Among existing spike detectors, the absolute value operator, the Nonlinear Energy Operator (NEO), the Multiresolution Teager Energy Operator (MTEO), Wavelet-Based Signal Processing and Template Matching are among the most common operators. Although they give good performances, most of these operators are too computationally intensive to be implemented in low-power embedded systems. Therefore, a powerful real-time spike detection technique optimized for utilization in low-power embedded systems is highly sought.

A further disadvantage of such systems is that microelectrodes used to record low-amplitude neuronal waveforms typically have high impedances (up to few $M\Omega$), which results in poor Signal-to-Noise Ratio (SNR), and which can result in the SNR changing over time. In order to reliably detect spikes in such cases, the supervision of an operator may be required in order to manually adjust a spike detection threshold. An automatic threshold calculation strategy based on an estimation of the SNR of the channel is thus also highly sought.

SUMMARY

According to an aspect, a method is provided for automatically determining a threshold for spike detection in an electrophysiological signal. The method includes the steps of estimating a standard deviation of noise in the electrophysiological signal using a Sigma-delta control loop, and automatically adjusting the threshold according to the estimated standard deviation.

In an embodiment, the Sigma-delta control loop is implemented in a digital system.

In an embodiment, estimating standard deviation includes the steps of: sampling the signal to obtain a current sample; storing the current sample along with previously obtained samples; providing a target value corresponding to a probability that the noise is above or below the standard deviation; and estimating the standard deviation by determining a value for which the current and previously obtained samples respect the target value.

In an embodiment, the method includes the step of taking an absolute value of the signal, and the target value corresponds to a probability that the noise is above or below the standard deviation in a half-normal distribution.

In an embodiment, the target value is approximately 31.7% and corresponds to a probability that the noise is above the standard deviation.

In an embodiment, adjusting the threshold according to the estimated standard deviation includes multiplying the estimated standard deviation by a predetermined factor to obtain the threshold.

In an embodiment, the method further includes the step of storing a predetermined number of previously obtained samples in a circular buffer.

In an embodiment, storing the current sample includes comparing the current sample with the estimated standard deviation and storing a binary value in the circular buffer corresponding to the current sample being above or below the estimated standard deviation.

In an embodiment, the method further includes the steps of: counting the values in the circular buffer corresponding to the previously obtained samples being greater than the estimated standard deviation; dividing the counted values by the circular buffer length and multiplying by 100 to obtain a percentage of previously obtained samples greater than the estimated standard deviation; subtracting the percentage from the target value to obtain an error signal; and integrating the error signal with a previously estimated standard deviation to obtain the estimated standard deviation.

According to an aspect, a digital system is provided for adaptively estimating a threshold for spike detection. The system includes a sampling module for sampling the signal; an absolute value operator module for taking an absolute value of the sampled signal; memory for storing an estimated standard deviation, a comparator module for comparing the absolute value of the sampled signal with the estimated standard deviation; a circular buffer for storing a fixed number of results from the comparator; a counter for counting results in the circular buffer which correspond to the absolute value of the sampled signal having a greater amplitude than the estimated standard deviation; an arithmetic module for calculating an error between the counted results and a percentage of samples which should be greater than the standard deviation in a half-normal distribution; an integrator for adjusting the estimated standard deviation based on the error; and a multiplication module for multiplying the estimated standard deviation by a predetermined constant to obtain the threshold.

According to an aspect, a digital system is provided for adaptively estimating a threshold for spike detection. The system includes a feedback loop configured to estimate a standard deviation of noise in an input signal, or a factor thereof, the feedback loop including: a digital integrator configured to generate a control signal corresponding to the estimated standard deviation of the input signal; a digital comparator configured to compare the control signal with the input signal and generate a PWM signal whose duty cycle encodes a number of input signal samples greater than the control signal; a demodulator configured to demodulate the PWM signal and obtain the duty cycle; and a subtraction module configured to obtain a difference between the duty cycle and a target value, said target value corresponding to a probability that the noise is above the standard deviation, said difference being provided as an input to the digital integrator.

In an embodiment, the demodulator includes a circular buffer configured to store a fixed set of previous values of the PWM signal and means for determining a percentage of the previous values corresponding previous input signal samples being greater than the control signal.

In an embodiment, the circular buffer includes a circular shift register.

In an embodiment, the means for determining a percentage includes a counter maintaining a count of the previous values of the PWM signal corresponding to previous input signal samples being greater than the control signal, said counter being configured to increment or decrement when a current value of the PWM signal differs from an oldest one of the fixed set of previous values stored in the circular buffer.

According to an aspect, a non-transient computer readable medium is provided for automatically determining a threshold for spike detection in an electrophysiological signal; the non-transient computer readable medium having instructions stored thereon for causing a computer to perform the steps of: estimating a standard deviation of noise in the electrophysiological signal using a Sigma-delta control loop, and automatically adjusting the threshold according to the estimated standard deviation.

According to an aspect, a method for determining a threshold for spike detection in a noisy signal in real-time is provided. The method includes the steps of: a) receiving the noisy signal; b) measuring a current instantaneous value of the noisy signal; c) estimating a current variability of noise in the noisy signal according to the current instantaneous value and a window of previous instantaneous values using a sigma-delta control loop; d) determining the threshold based on the estimated variability of the noise; and e) repeating steps a) through d) to update the current estimate of the variability of the noise and adjust the threshold in real-time as the noisy signal changes.

In an embodiment, the noisy signal is an electrophysiological signal.

In an embodiment, estimating the variability of the noise comprises estimating a standard deviation of the noise, or a factor of the standard deviation and determining the threshold comprises scaling the estimated standard deviation, or the factor of the standard deviation, by a predetermined factor.

In an embodiment, estimating the standard deviation, or the factor of the standard deviation, includes: providing a target probability corresponding to a probability that the noise is greater than the standard deviation, or the factor of the standard deviation; and adjusting the estimated standard deviation, or the estimated factor of the standard deviation, such that a ratio of the current and previous instantaneous values greater than the estimated standard deviation, or the factor of the estimated standard deviation corresponds to the target probability.

In an embodiment, estimating the standard deviation, or the factor of the standard deviation, includes: providing a target probability corresponding to a probability that the noise is less than the standard deviation, or the factor of the standard deviation; and adjusting the estimated standard deviation, or the estimated factor of the standard deviation, such that a ratio of the current and previous instantaneous values less than the estimated standard deviation, or the factor of the estimated standard deviation corresponds to the target probability.

In an embodiment, the target probability is approximately 31.7%.

In an embodiment, the method includes maintaining a counter corresponding to the ratio of the current and previous instantaneous values greater than, or less than, the estimated standard deviation, or the factor of the standard deviation, and, following each measurement of the instantaneous value, updating the counter and incrementally adjusting the estimated standard deviation, or the factor of the standard deviation, according to an error between the counter and the target probability.

In an embodiment, the method further includes maintaining a buffer of a predetermined length, the buffer comprising results of comparisons between the current and previous instantaneous values and the estimated standard deviation, or the factor of the estimated standard deviation; and wherein upon measuring the current instantaneous value: if the instantaneous value is less than the estimated standard deviation and the oldest comparison in the buffer corresponds to an oldest value in the window being greater than or equal to the standard deviation, incrementing the counter; and if the instantaneous value is greater than or equal to the estimated standard deviation and the oldest comparison in the buffer corresponds to an oldest value in the window being less than the standard deviation, decrementing the counter.

In an embodiment, upon measuring the current instantaneous value, the method includes performing the steps of: calculating an error between the target probability and the ratio of the current and previous instantaneous values greater than or less than the estimated standard deviation, and incrementally adjusting the estimated standard deviation by adding thereto the error multiplied by a predetermined factor.

In an embodiment, multiplication by the predetermined factor is approximated by a bit shifting operation.

In an embodiment, the method further includes taking an absolute value of the current and previous instantaneous values, and estimating the variability of the noise amplitude comprises modelling an amplitude of the noise according to a half-normal distribution.

In an embodiment, estimating the current variability of the noise includes: comparing the current instantaneous value with the current estimated variability, and maintaining comparison results for the window of previous instantaneous values; calculating a ratio of positive comparison results to negative comparison results; calculating an error between the ratio and a predetermined target probability; and adjusting the current estimate of the variability to reduce the error.

In an embodiment, the method further includes detecting spikes in the noisy signal by identifying instantaneous values of the noisy signal above the determined threshold.

In an embodiment, the method further includes operating a brain-machine interface (BMI) using the detected spikes, the detected spikes corresponding to action potential in an electrophysiological signal.

According to an aspect, a non-transitory computer readable storage medium is provided. The storage medium includes instructions that cause a processing unit of a system for determining a threshold for spike detection in a noisy signal in real-time to: a) receive the noisy signal; b) measure a current instantaneous value of the noisy signal; c) estimate a current variability of noise in the noisy signal according to the current instantaneous value and a window of previous instantaneous values using a sigma-delta control loop; d) determine the threshold based on the estimated variability of the noise; and e) repeat steps a) through d) to update the current estimate of the variability of the noise and adjust the threshold in real-time as the noisy signal changes.

According to an aspect, a low power digital system for determining a threshold for spike detection in a noisy signal in real-time is provided. The system includes: an input for receiving and sampling the electrophysiological signal; a comparator configured to receive a value of the sample and compare the value with a control signal corresponding to an estimate of a variability of noise in the signal, the comparator generating a pulse width modulated (PWM) signal with a duty cycle encoding results of the comparison; a demodulator operatively connected to the comparator, the demodulator being configured to demodulate the PWM signal and obtain a duty cycle thereof; an arithmetic module operatively connected to the demodulator, the arithmetic module being configured to generate an error signal corresponding to an error between the duty cycle and a target probability; an integrator operatively connected to the arithmetic module, the integrator being configured to generate the control signal and estimate the variability of the noise in the signal by reducing the error signal; and a gain module operatively connected to the regulator, the gain module being configured to receive the control signal and multiply it by a predetermined factor to obtain the threshold for spike detection.

In an embodiment system includes an absolute value operator configured to compute an amplitude of the sampled electrophysiological signal, said amplitude corresponding to the value of the sample.

In an embodiment, the comparator is configured to generate a PWM signal with a duty cycle encoding a number of samples which are greater than or less than an estimated standard deviation of the noise in the signal.

In an embodiment, the demodulator is configured to demodulate the PWM signal over a window of previous comparison results.

In an embodiment, the PWM signal is stored in a circular buffer of a fixed size, the buffer size corresponding to a size of the window of previous comparisons which are to be demodulated.

In an embodiment, the buffer size is between 32 and 8192 bits.

In an embodiment, each bit of the buffer corresponds to a binary result of the comparator following comparison of a given sample value with the control signal.

In an embodiment, the demodulator includes a counter configured to maintain a count of the binary comparison results in the circular buffer.

In an embodiment, the arithmetic module is configured to subtract the count from the target probability multiplied by the buffer length, thereby generating the error signal corresponding to the error between the duty cycle and the target probability multiplied by the buffer length, and wherein the predetermined factor in the integrator accounts for the buffer length, thereby allowing for the error signal to be generated without a division operation.

In an embodiment, the integrator is configured to obtain a current estimate of the variability of the noise by adding a previous estimate of the variability of the noise with the error signal multiplied by a predetermined factor.

In an embodiment, the predetermined factor multiplying the error signal is approximated by applying a bit shifting operation to the error signal.

In an embodiment, the comparator, demodulator and integrator are implemented exclusively using addition and comparison and multiplication operations, and preferably exclusively using addition and comparison operations.

In an embodiment, at least some of the multiplication operations are approximated using bit shifting operations.

In an embodiment, the target probability is approximately 31.7% and corresponds to a probability of noise being greater than one standard deviation in a half normal distribution.

In an embodiment, the system further includes a spike detection module configured to detect spikes in the noisy signal corresponding to samples having values greater than the determined threshold.

In an embodiment, an output of the spike detection module is operatively connected to a computing unit, the detected spikes serving as an input to operate the computing unit as part of a brain-machine interface (BMI).

In an embodiment, noisy signal is an electrophysiological signal, and the input includes an electrode for interfacing with biological tissue and acquiring the electrophysiological signal therefrom.

BRIEF DESCRIPTION OF THE DRAWINGS

FIG. 8 is a table illustrating a comparison of detection rates using a synthetic neural signal and different spike detection approaches.

FIG. 9 is a table illustrating a comparison of microcontroller unit (MCU) execution time for different spike detection methods including one channel at 8 MHz.

FIG. 10 is a table illustrating a comparison of the number of operations required to carry out different spike detection methods.

DETAILED DESCRIPTION

Figure 1:
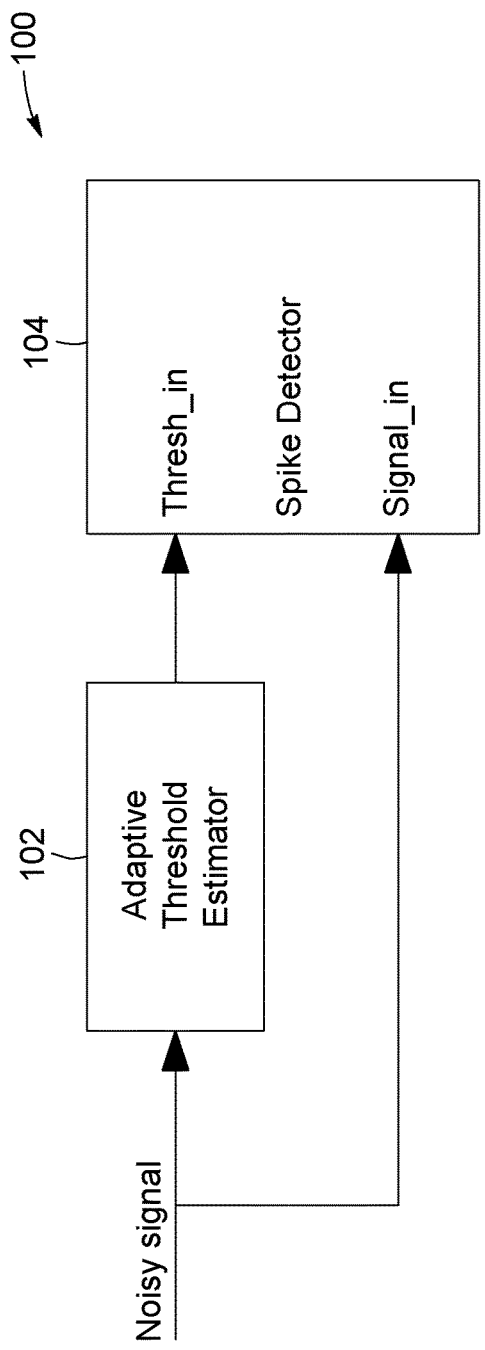
FIG. 1 is a block diagram schematically illustrating the basic components of a spike detection system, according to an embodiment.

With reference to FIG. 1, a system 100 for detecting spikes in noisy signals is provided. Broadly speaking, the system includes two main modules: (1) an adaptive threshold estimator 102 and (2) a spike detector 104. Although not illustrated, it should be appreciated that an output of the spike detector (i.e. a signal indicating detected spikes) can be provided to a computing unit, such as a computer, microcontroller, programmable logic device, application-specific integrated circuit (ASIC) or other such devices, for example to serve as an input to operate the computing unit, for example as part of a brain-machine interface.

In the present configuration, the adaptive threshold estimator 102 processes a signal input from a channel and determines an optimal threshold value which can be used to reliably distinguish between a signal spike and noise in the channel. In the present context a "spike" can correspond to a pulse or a short voltage transient in the signal. Such a spike can be identified in a noisy signal, for example, by modelling noise in the signal and identifying statistical outliers. In the following description, the signal input corresponds to an electrophysiological signal acquired from biological tissue, for example using an electrode. In this context, a spike in the signal can correspond to action potential, and detected spikes can be provided as an input to a computing unit for operating a BMI. It should be appreciated, however, that other types of signals can also be processed in a similar manner. For example, telecommunication signals, or any other type of signal which contains random noise therein can be processed in a similar manner. The threshold value determined by the threshold estimator 102 is then fed into a spike detector 104. The spike detector uses said threshold to identify signal spikes in the channel.

As will be understood from the following description, the threshold estimator is "adaptive" in that it is configured to process the channel input on-the-fly and in substantially real-time so that the threshold can be adjusted as the properties of the signal in the channel change, thereby allowing the system to achieve high detection rates. For example, as noise in the signal increases, the threshold can be raised in order to reduce false detection rates. Similarly, as noise in the signal decreases, the threshold can be lowered to more accurately identify action potential. As will be further understood, the operations performed in the threshold estimator 102 and spike detector 104 can be implemented using relatively simple operations, and using strictly digital components, making the present configuration ideal for low-power and small form-factor applications.

1. Spike Detection Method

In the present embodiment, the spike detector 104 receives the measured noisy signal at a first input ("Signal_in") and receives the threshold determined by the adaptive threshold estimator 102 at a second input ("Thresh_in"). The spike detector 101 takes an absolute value of the measured signal (thereby calculating its amplitude) and compares it with the threshold in order to detect if a spike has occurred, according to the following operator:

$$y(n) = |x(n)|, \begin{cases} \text{if } y(n) > \text{threshold, a spike is detected} \\ \text{else, no spike is detected} \end{cases}$$

Where $x(n)$ represents the $n^{th}$ sample.

Such an operator can offer low-complexity and good performances, which are preferable features for utilization in low-power devices.

It should be understood that in an alternate embodiment, the spike detector can compare the channel input with a threshold, without taking the absolute value of the signal.

2. Adaptive Threshold Method

In the present embodiment, the absolute value operator in the spike detector 104 works alongside a threshold whose value is determined adaptively in the threshold estimator 102 according to the amplitude of the noise in the channel.

Preferably, the adaptive threshold estimator 102 determines the threshold based on a parameter which quantifies the variability of noise in the signal, such as the standard deviation ($\sigma$). In the present embodiment, the adaptive threshold estimator 102 relies on the statistical properties of the half-normal distribution to estimate the variability by approximating the noise in the channel to a white Gaussian noise. When the signal is folded positively (with DC component removed) by the absolute value operator, the amplitude of the white Gaussian noise follows a half-normal distribution. As can be appreciated, by modelling the noise in this fashion, the entirety of the noise (i.e. both positive and negative values) can be taken into account when estimating the threshold. This can allow for more precision when combined with a spike detector which also operates using the absolute value of the signal, as opposed to existing methods which merely consider positive values of the signal for detecting spikes.

With the given probability density function of the noise distribution, the probability that the amplitude of the additive noise exceeds the standard deviation ($\sigma$) is 31.7%:

$$31.7\% = 100\% - \int_0^\sigma \frac{1}{\sigma} \sqrt{\frac{2}{\pi}} e^{-\frac{x^2}{2\sigma^2}} dx \times 100\%$$

Figure 2:
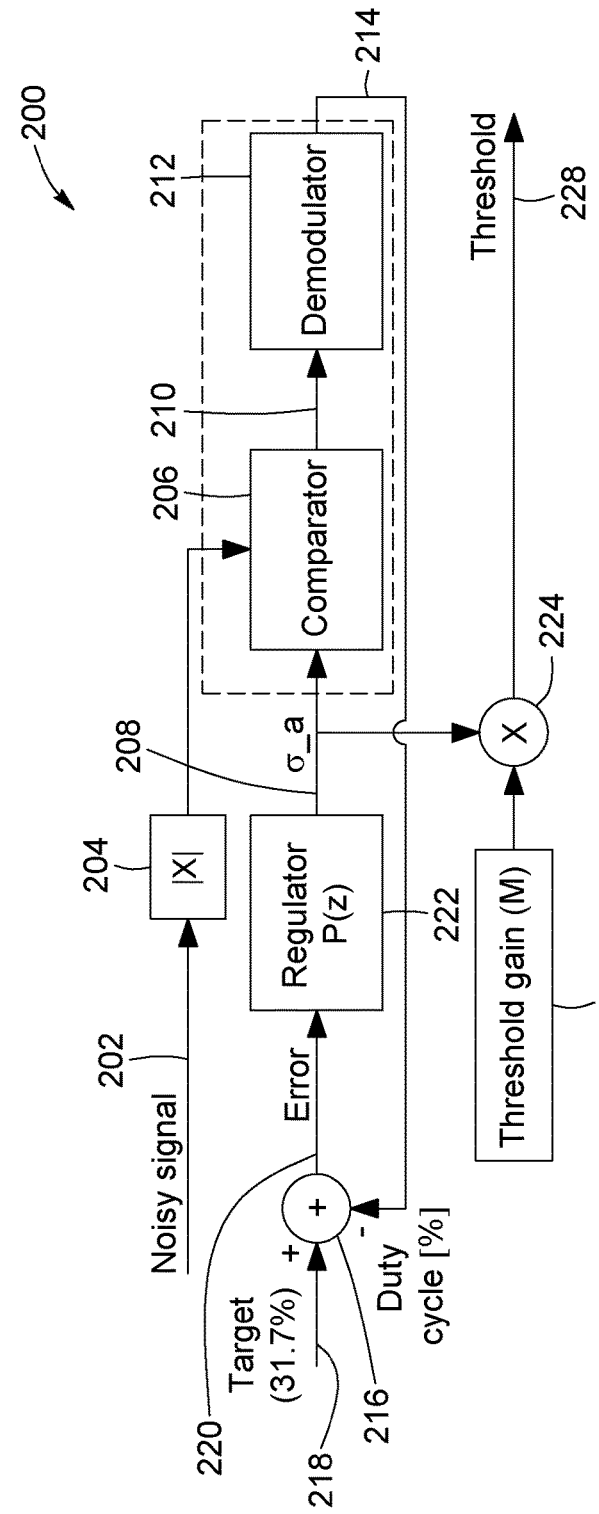
FIG. 2 is a block diagram schematic illustrating a Sigma-Delta control loop for estimating a threshold for spike detection, according to an embodiment.

With reference to FIG. 2, an embodiment of the adaptive threshold estimator is shown whereby the estimator is implemented as a control loop 200 which exploits the statistical properties described above for determining a threshold value. In the illustrated control loop 200, the standard deviation ($\sigma$) of the noise amplitude is estimated by using a feedback control loop based on a Sigma-delta modulator. In this sense, the spike detection method implemented by the adaptive threshold estimator can be referred to as a "SDCLT", or Sigma-delta Control Loop Threshold.

As illustrated in FIG. 2, the control loop comprises an input 202 for receiving and sampling and/or measuring an instantaneous value of the noisy signal. The sampled signal is provided to an absolute value operator 204 which folds the sample positively, effectively measuring the amplitude of the sample. A comparator 206 receives the sample and compares it with a control signal 208 corresponding to an estimate of the standard deviation ($\sigma\_a$). The comparator 206 generates a pulse width modulated (PWM) signal 210 with a duty cycle encoding the number of samples which are greater than the estimated standard deviation ($\sigma\_a$). The PWM signal 210 is fed into a demodulator which demodulates the signal to obtain a duty cycle 214 thereof, the duty cycle thus corresponding to a percentage or ratio of previous samples which are greater than the estimated standard deviation ($\sigma\_a$). An arithmetic module 216 subtracts the duty cycle 214 from a target probability 218 to generate an error signal 220. In the present case, the target probability 218 corresponds to the probability of noise being greater than one standard deviation in a half-normal distribution, and is thus approximately 31.7%. The error signal 220 thus represents an error between the expected ratio of samples above the actual standard deviation and the actual ratio of samples above the estimated standard deviation. The error signal 220 is then fed into an integrator or regulator 222 which attempts to reduce the error by adjusting the estimated standard deviation (i.e. the control signal 208) accordingly. The output (i.e. the control signal 208 corresponding to the estimated standard deviation) of the integrator 222 (or regulator) is used to determine the threshold value 228. More particularly, the control signal 208 is fed into a gain module 224 which multiplies the control signal 208 by a predetermined factor (or gain) 226 to obtain the final threshold 228.

The above-described control loop 200 corresponds to a Sigma-delta control loop where the number of samples whose amplitudes exceed the standard deviation is estimated from the process under control. The process compares the absolute value of the channel input (i.e. a noisy signal) with the control signal, and demodulates the generated pulse-width modulation (PWM) output to estimate the number of samples whose absolute value is greater than the control signal. The output of the comparison gives a PWM signal whose duty cycle encodes the number of samples whose absolute value is greater than the control signal.

In each iteration, the integrator tries to reduce the error between the target value, which is taken as 31.7%, to reach an approximation of the standard deviation, and the output of the process. Once the control loop reaches its steady state, the output signal of the integrator gives an approximation of the standard deviation.

Once an estimate of the standard deviation is obtained at the output of the integrator, it can be multiplied by a constant M to give the value of the threshold. The proposed control loop is similar to a first order Sigma-delta but differs since it uses a demodulator (a digital filter) in the feedback path, and by comparing the magnitude of the new incoming samples directly with the output of the integrator.

Although in the present embodiment the target value is chosen such that the output approximates the standard deviation, it should be understood that the target value could be chosen so that it approximates any factor of the standard deviation, or any factor of any parameter which can represent the variability of the noise in the signal. Since the output is multiplied by a constant M, the constant can be adjusted according to the parameter being estimated in order to obtain the desired threshold size. For example, if the desired threshold is 2$\sigma$, the target value can be 31.7%, and M can be 2. The target value can alternatively be 61.7% (i.e. to reach an approximation of $\sigma/2$, found by solving:

$$100\% - \int_0^{\sigma/2} \frac{1}{\sigma}\sqrt{\frac{2}{\pi}} e^{-\frac{x^2}{2\sigma^2}} dx \times 100\%),$$

with M being 4. Other combinations are also possible.

It should also be understood that in the presently described embodiment, the feedback loop is configured such that the PWM signal encodes the number of samples whose absolute value is greater than the control signal. In an alternate embodiment, the feedback loop can be inversed, and could instead encode the number of samples whose absolute value is lower than the control signal. In such a scenario, in order to estimate the standard deviation, the target value can instead be selected as 68.3%.

In an alternate embodiment, the adaptive threshold strategy can rely on the statistical properties of different types of distributions, such as the normal distribution. For example, in the spike detector, if the channel input is not folded by an absolute value operator when comparing it to a threshold, the noise in the channel can be modeled as white Gaussian noise which follows a normal distribution. In such a scenario, the probability that the noise amplitude exceeds the standard deviation is approximately 15.9%. The control loop can thus be configured with a target value of 15.9% to approximate the standard deviation of the noise according to the normal distribution.

3. Digital Implementation

The above described methods for spike detection and adaptive threshold are preferably implemented in a low-power system, which is preferably entirely digital. In order to do so, the methods can be broken down into steps which require the use of basic logic components such as RAM memory blocks, adders, comparators, and shift registers. In this way, the threshold estimation and spike detection can be implemented in programmable logic devices, such as field programmable gate arrays (FPGA) or application-specific integrated circuits (ASIC) using very low hardware resources. They can also be implemented as a software program product for execution on a general-purpose processor.

With reference to FIG. 2 the integrator 222 can be implemented using basic logic components by treating it as a sum of Riemann:

$$I_n = I_{n-1} + G \times T \times E$$

where G is the gain of the integrator, T the sampling period, E the error relative to the reference 220 and $I_n$ is the integrator value at time n. G and T are known in advance, thus the multiplication can be approximated using a shifting operation.

The output of the integrator 222 $I_n$ is the approximation of the standard deviation 208, $\sigma_a$. This value is compared with the absolute value of the current sample using the comparator 206 in order to generate the PWM signal 210. The comparator 206 can generate the PWM signal 210 by setting its output to 1 if the absolute value of the current sample is over $\sigma_a$, and 0 otherwise.

The PWM signal 210 can be stored in a RAM memory block so that it can be subsequently demodulated. The RAM memory block can be implemented as a circular buffer which stores a fixed number L of previous comparison bits in memory. In so doing, the standard deviation can be estimated based on a fixed window of comparisons of previous samples of the signal. In an embodiment, the buffer can store 128 comparison bits, but this can vary according to the system requirements. For example, in other embodiments, a 256 bit buffer can be used. Preferably, the buffer size is in a range of approximately 32 to 65,536 bits and preferably still in a range of approximately 32 to 8,192 bits. In some embodiments, the spike detector can be configured to detect multiple channels, such as 32 channels, and the RAM can therefore be split into 32 segments to serve as multiple circular buffers, with one circular buffer per channel.

Demodulating the PWM signal 210 can involve reading from the circular buffer. Before writing a new comparison bit in the buffer, the oldest bit at the beginning of the circular buffer is retrieved. If the current comparison bit is 1 and the oldest bit is 0, a counter is incremented. If the current comparison bit is 0 and the oldest bit is 1, the same counter is decremented. In all other cases, the value of the counter remains unchanged. This counter holds the sum of all the bits in memory which, when divided by the circular buffer length L and multiplied by 100, represents the percentage of the samples whose amplitudes are over $\sigma_a$. This percentage will be referred to hereafter by the letter P, and corresponds to the duty cycle 214 of the PWM signal 210. The error E 220 calculated by the arithmetic module 216 can therefore be presented as:

$$E = \text{target\_value} - P/L.$$

Because the circular buffer length L is known in advance, and to prevent the use a division circuit, the target value is set as 31.7% multiplied by the circular buffer length. Therefore, the operation:

$$E = \text{target\_value} - P/L$$

becomes:

$$L \times E = L \times \text{target\_value} - P.$$

The factor L that is multiplying the error E can be merged with the integrator gain and approximated with a shifting operation. For example, the integrator output can be written as:

$$I_n = I_{n-1} + K \times L \times T \times E$$

Where G=K×L. The result of L×target_value is also known in advance, and can therefore be hard coded. For example, for a buffer length L of 128 bits, and a target value of 31.7%, the result is 128×0.317=40.576 which can be approximated by the integer 41. The bit counter and the last integrated value are stored in RAM memory alongside the circular buffer for each channel.

Once the integrator output $I_n$ is obtained, the threshold is obtained by multiplying said output by a factor M using the gain module 224. For example, the factor M can be chosen as 2, causing the threshold to be two times the estimated standard deviation ($2\sigma_a$). In such a scenario, the multiplication Threshold=$I_n \times M$ can be implemented using a simple shifting operation.

As can be appreciated, in the present embodiment, if the desired threshold size does not correspond to the standard deviation multiplied by an exponent of 2 (i.e. $2\sigma_a$, $4\sigma_a$, $8\sigma_a$ etc.), the factor M cannot be implemented using a simple shifting operation. For example, if the desired threshold size is $3\sigma_a$, M would need to be implemented as a multiplication operation to achieve a multiplication factor of 3. However, in alternate embodiments, such a multiplication can be avoided by configuring the integrator to estimate a factor of the standard deviation rather than exactly one standard deviation. This factor can be chosen such that M is an exponent of 2, allowing the threshold to be obtained by simply shifting the estimated value. For example, in an embodiment having a buffer length L of 256 bits, a threshold of $3\sigma_a$ can be obtained without a multiplication by 3 by estimating $0.75\sigma_a$ instead of $\sigma_a$. In this scenario, the probability of noise being above $0.75\sigma_a$ is approximately 45.7%. L×target_value is therefore 256×0.457=116.992, which can be approximated as 115. $3\sigma_a$ can thus be obtained using the factor M=4, as $3\sigma_a = 4 \times 0.75\sigma_a$, allowing to obtain a threshold of $3\sigma_a$ with M still being implemented as a shifting operation.

Figure 3:
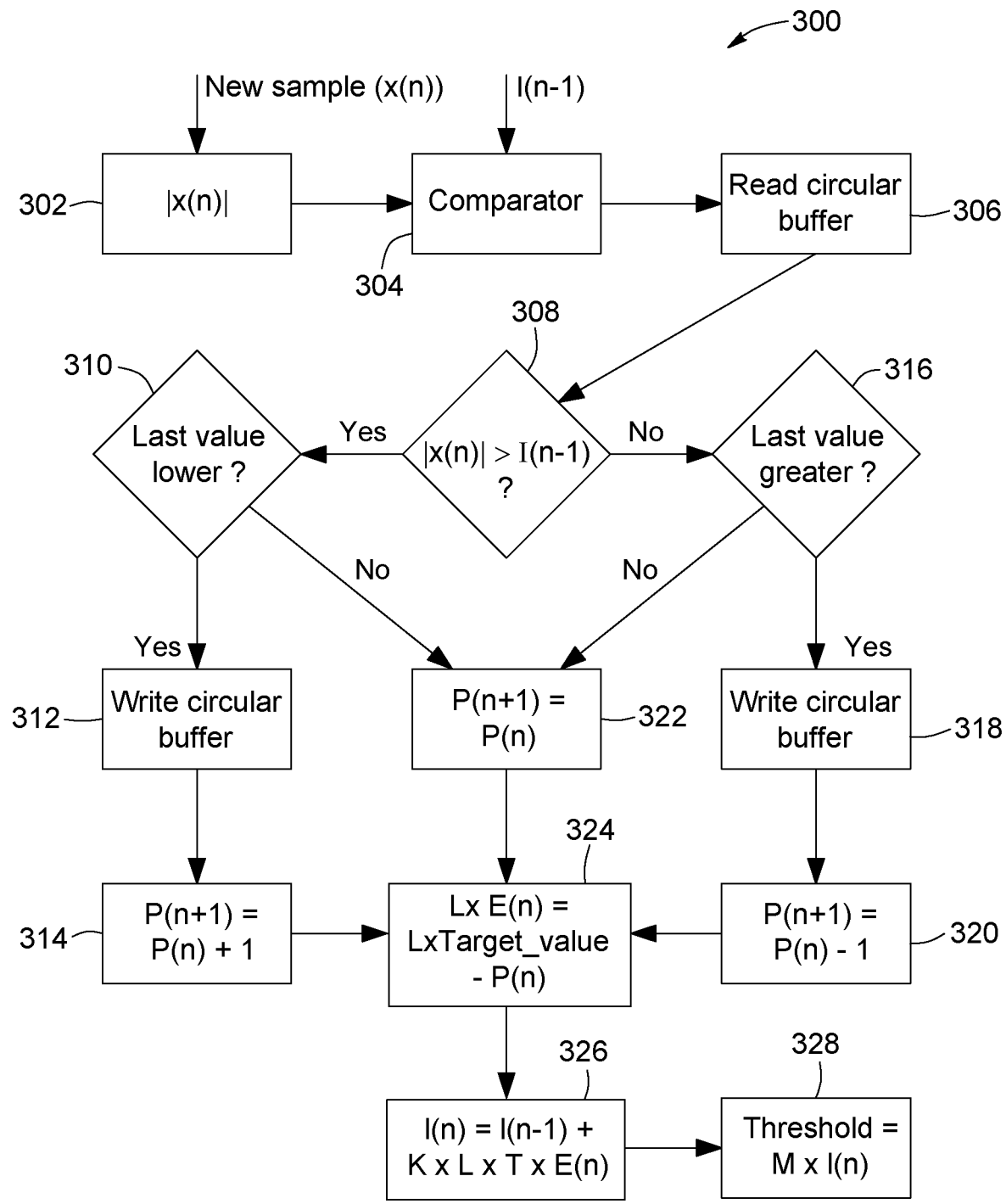
FIG. 3 is a flow chart illustrating a process for estimating a threshold for spike detection using the Sigma-Delta control loop of FIG. 2.

With reference now to FIG. 3, an embodiment of a method 300 for determining a threshold for spike detection in real-time is provided. The method 300 can be implemented using the basic logic components described above, making it viable in a low power system. In the illustrated method, x(n) refers to a value of the signal sample at time n, i.e. the current cycle. Time n−1 refers to a previous cycle, while n+1 refers to a next cycle. Similarly, I(n) refers to the output of the integrator, P(n) refers to a count of the number of previous samples above the estimated standard deviation, and E(n) refers to the error between P(n) and the expected number of previous samples above the standard deviation in the half-normal distribution.

In a first step 302, the electrophysiological signal is received and its instantaneous value x(n) is measured. In the present embodiment, measuring the instantaneous value comprises measuring an amplitude of the instantaneous value by taking an absolute value thereof |x(n)|. In this fashion, subsequent steps for determining the threshold take into account the entirety of the signal (i.e. both positive and negative values).

In a next step 304, the instantaneous value |x(n)| is compared with the most recent estimate of the standard deviation, i.e. the output of the integrator from the previous cycle I(n−1). In the present embodiment, the result of the comparison is binary, meaning if |x(n)|>I(n−1), the comparator output is 1, whereas the comparator output is 0 otherwise.

The result of this comparison can then be used to update the count of samples above the estimated standard deviation P(n). More particularly, this involves reading a last value of a circular buffer containing results from previous comparisons in step 306, and comparing the last value with the result of the current comparison. In steps 308 and 310, if the result of the current comparison is 1 (i.e. |x(n)|>I(n−1)) and the oldest comparison in the circular buffer is 0, the count P(n) needs to be increased. Accordingly, the oldest value in the buffer is overwritten with the latest comparison result in step 312, and the count for the next cycle P(n+1) is incremented in step 314. Alternatively, in steps 308 and 316, if the result of the current comparison is 0 (i.e. |x(n)|<=I(n−1)) and the oldest comparison in the circular buffer is 1, the count P(n) needs to be decreased. Accordingly, the oldest value in the buffer is overwritten with the latest comparison result in step 318, and the count for the next cycle P(n+1) is decremented in step 320. In both steps 310 and 316, if the result of the current comparison is the same as the result of the oldest comparison, the count P(n) remains the same, and P(n+1) =P(n) in step 322.

Once the count P(n) has been updated, it can be used in order to calculate the error E(n) between the expected count and the actual count P(n) in step 324. As discussed above, to avoid a division operation, L*E(n) is calculated. In step 326 the variability of the noise (in this case the standard deviation) is estimated by calculating the output of the integrator I(n). Finally, in step 328, the threshold is determined based on the estimated variability, in this case by multiplying the output of the integrator I(n) (i.e. the estimated standard deviation) by a predetermined factor M. As can be appreciated, the steps described above can be repeated to allow the feedback loop to reach a steady state, and to allow the threshold to be further adjusted in real-time as characteristics of the input signal change.

Figure 4:
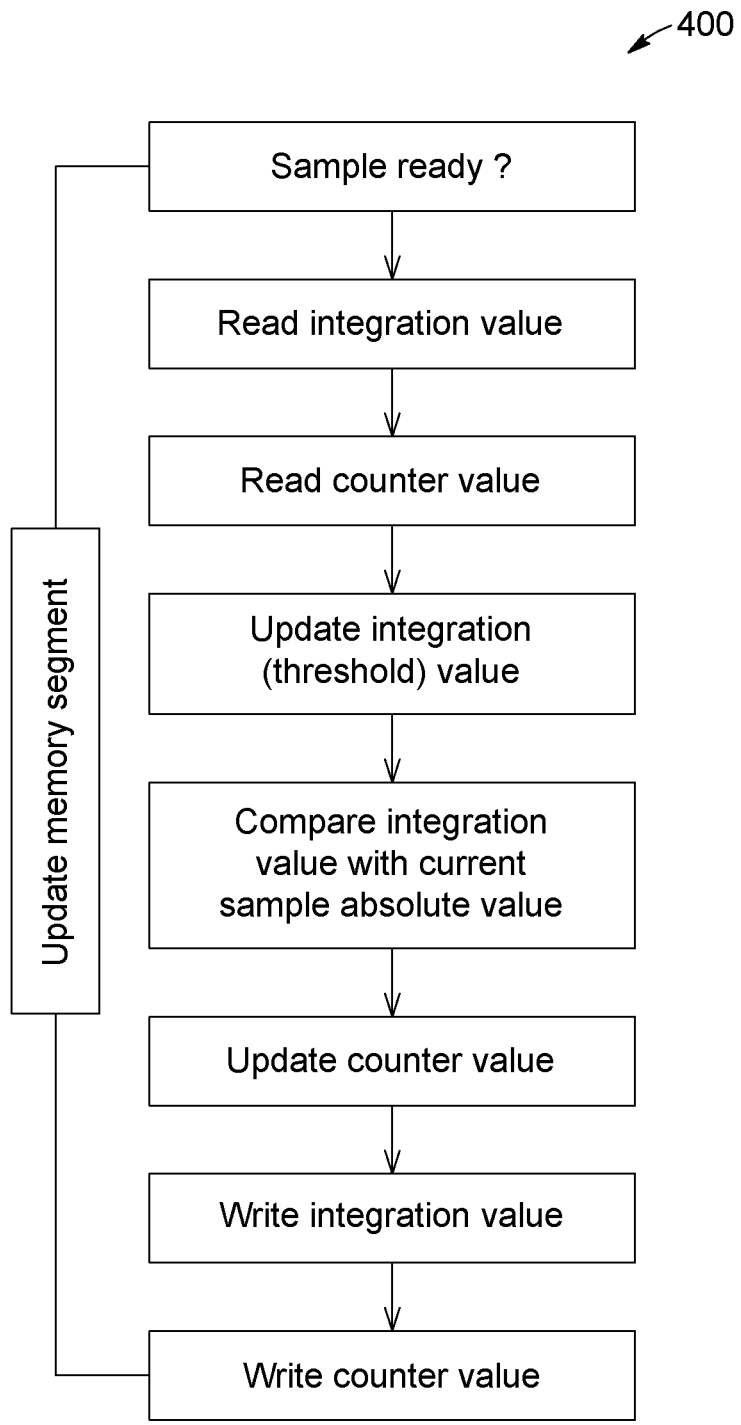
FIG. 4 is a flow chart illustrating steps in a digital implementation of the process for estimating a threshold for spike detection of FIG. 3.

In an embodiment, the steps described above can be carried out sequentially, as summarized in the method 400 of FIG. 4. In the illustrated embodiment, each threshold calculation requires only nine clock cycles per channel. As such, the operations can be performed using a low clock frequency. For example, where threshold estimation and spike detection is being carried out on 32 channels with a sampling rate of 20 kHz, the operations can be performed using a low clock frequency of only 5.76 MHz.

4. Experimental Configurations and Results
Low-Power Adaptive Spike Detector

Figure 5A:
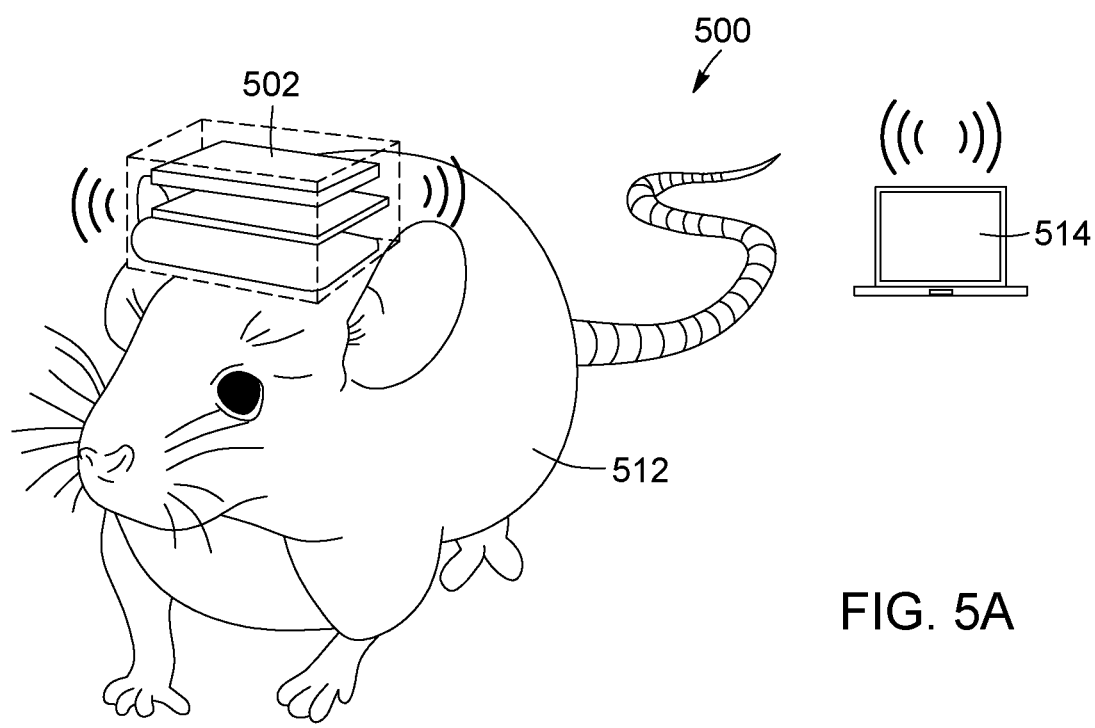
FIG. 5A is a schematic overview of a wireless optogenetic platform used in a test configuration to characterize an embodiment of a spike detection system.
Figure 5B:
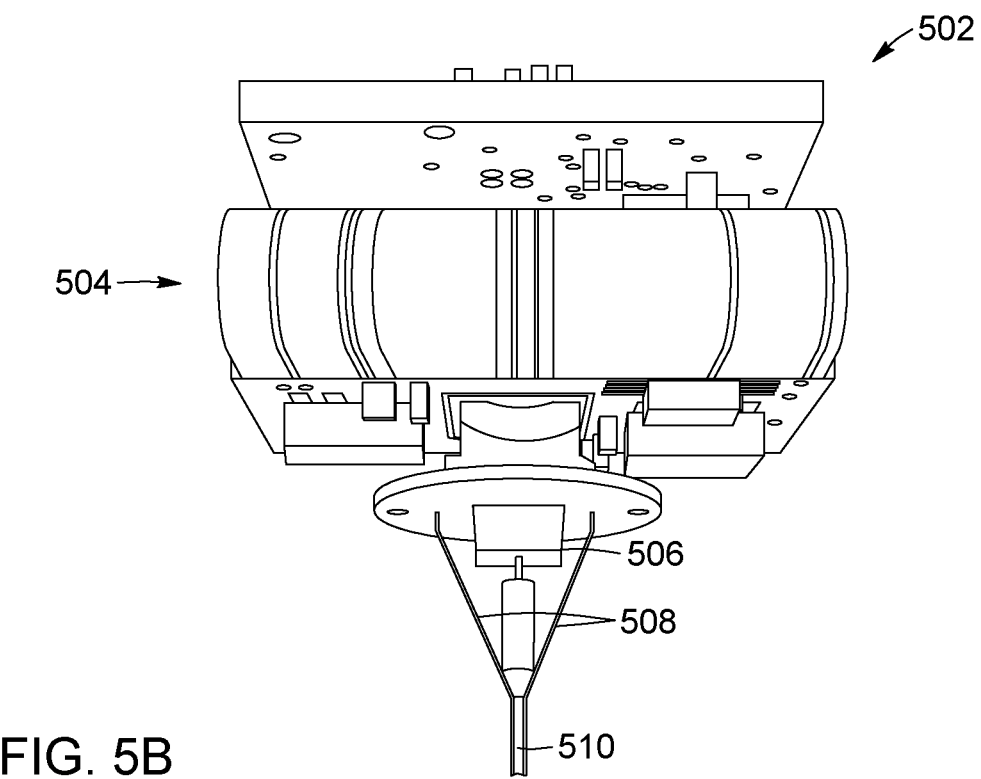
FIG. 5B is a perspective view of a headstage used in the optogenetic platform of FIG. 5A, according to an embodiment.

FIGS. 5A and 5B show an overview of a wireless optogenetic platform 500 employed to characterize an embodiment of the threshold estimator and spike detector discussed above. The platform 500 includes an implantable module 502 which includes a headstage 504 comprising digital circuitry for implementing the threshold estimator and spike detector. The implantable module 502 further includes LEDs 506 and optical fiber 510 for optically stimulating cells, and microelectrodes 508 for acquiring electrophysiological signals generated by the cells in response to the optical stimulation. In the present embodiment, the implantable module 502 is implanted in brain tissues of a transgenic mouse 512, and communicates wirelessly with a base station 514 for transmitting detected action potential (AP) thereto for analysis.

The present embodiment of the optogenetic platform 500 was entirely built using commercial of the shelf (COTS) components. It consists of five main building blocks: 1) the implantable module which holds the microelectrodes and the LEDs, 2) a low-noise 2-channel analog front-end (AFE) having a bandwidth lying between 300 Hz and 6 kHz and an overall gain of 5000 VN, 3) a 2.4-GHz nRF24L01+ wireless transceiver from Nordic Semiconductors, Norway, having a maximum data rate of 2 Mbps, 4) a power management unit (PMU) and 5) a low-power Microcontroller Unit (MCU) MSP430F5328 from Texas Instruments, USA. The MSP430 MCU family has been used in many biomedical monitoring applications which makes it perfectly suited for benchmarking the present spike detector. In such a system, the MCU is in charge of sampling the filtered and amplified neural signal at a rate of 20 kHz, with a resolution of 12 bits. Sampling is triggered by a timer, and the digitized samples are transferred from an ADC inside the MSP430 to a circular buffer using a DMA module. Packets of 32 bytes are transferred to the transceiver via a SPI bus using another DMA channel, so the MCU can focus on running the spike detector algorithm in the meantime. The operating frequency of the MCU was set to 8 MHz to address the trade-off between speed and power consumption.

The spike detection algorithm was implemented using an absolute value operator whose output is compared with an adaptive threshold value. Each new incoming sample is stored within the RAM memory of the MCU using the DMA controller while the ADC conversions and DMA transfers are automatically triggered by a timer. The MCU wakes up from sleep mode when 16 new samples become available in the buffer. When a detection occurs, the 16 bytes of the spike window that precede the detection point are transmitted within a 32 bytes packet. Then, to avoid multiple detection of the same spike, the detection is deactivated until 32 new bytes are received and sent within two packets. As to speed up the packet transfer and to let more time for threshold calculation, the 12-bits samples are stored within two bytes without packing the remaining four bits. Since the packets are transferred to the transceiver via an SPI link fed by a DMA module, the cost of transmitting more data has no significant impact on the allowable algorithm execution time.

In order to track any changes in the input signal and the noise, the thresholding algorithm must be executed at regular intervals by the MCU. For a system including two recording channels, each having a sampling frequency of 20 kHz, the maximum execution time (without overhead) is of 25 µs. It is worth noting that most MCU are not optimized to perform highly demanding arithmetic operations, and that most of them don't possess a multiplier or a division unit. Thus, those operations have been avoided in this implementation. Consequently, the proposed hardware implementation uses only additions, comparisons and it approximates the multiplications and the divisions by bits shifting operations.

To reconstruct the original input signal, a time stamp is appended to each packet. To do so, a 16-bit timer is used to cause an interrupt into the MCU every millisecond as to increment a 16-bit counter. The value of the counter is concatenated with the value of the timer (only 13 bits are necessary to cause an interrupt at every millisecond with a 8 MHz clock), which gives a 29-bits time stamp precision with an upper bound of 65.5 seconds. The 29 bits are concatenated with the first eight 12-bits samples of the first packet of each spike. On the base station side, a 65.5 second timer is used to replace the detected spikes in the right 65.5 seconds time bin in order to put the spikes in the right order.

Since the incoming packets can belong either to channel one or to channel two, the channel number and the packet number are concatenated with the 9th and 10th samples of the packet respectively. The packet number is encoded on four bits and is used to detect a packet loss. When a packet loss occurs, all the packets belonging to the lost spike are simply discarded.

Results and Discussion

This section presents the measured results of the above-described implementation, and a comparison with other thresholding methods used alongside the absolute value operator. Synthetic neuronal signals with different SNRs were played at the input of the detector using an arbitrary function generator to test the proposed method. The SNR was measured as follows:

$$SNR_{dB} = \log\left(\frac{P_{ap}}{n}\right)$$

where $P_{ap}$ is the power of all action potential (AP) waveforms included in the signal, and $P_n$ is the power of the noise, without the APs. The input signal was attenuated using a resistor voltage divider to produce a neuronal signal within 160 pV peak to peak maximum. Other methods were simulated in Matlab with the same signals for comparison.

The implemented spike detector uses the following parameters: The fixed value of L×target value (128×0.317) parameter is approximated by the integer 41. The G×T parameter is approximated by shifting the bits nine positions on the right, which is achieved by considering the nine last bits of the current integer value as being fractional. Finally, the threshold gain M is approximated by shifting the bits by eight positions, which is equivalent to a multiplication by 2 with the last nine bits of the integer value being fractional.

To give an insight on the excellent performance of the proposed method, the proposed detector is compared with its non-optimized counterpart implemented in Matlab without any efficiency optimization. Other algorithms are also implemented in Matlab for comparison. One of such algorithms involves computing the root mean square (RMS) from a finite window of samples:

$$X_{RMS} = \sqrt{\frac{1}{n}\sum_{i=1}^{n} x_i^2}$$

Where $x_i$ is the $i^{th}$ band pass filtered sample. The threshold value is evaluated as a multiple of $X_{RMS}$, multiplied by four in order to obtain the best detection results. The window width employed in the calculation of the threshold value was set to 128 samples. Another method, used within the popular freeware Wave Glus, calculates the median of the absolute deviation (MAD) as follows:

$$\delta = \text{median}\left\{\frac{|x|}{0.6745}\right\}$$

where x is the band-pass filtered signal. The threshold is evaluated as a multiple of 6, which is multiplied by four (same as Wave Glus). It should be noted that Wave Glus can only be used offline.

In addition to the MAD operator, which is calculated over the whole signal (denoted MAD1), a MAD operator can also be calculated over a 1024-sample sliding window. This latter algorithm (denoted MAD2) is extremely computationally demanding, but can potentially be implemented in an FPGA or in a powerful MCU using an algorithm like QuickSort to find the median of a sliding window of samples.

Figure 6:
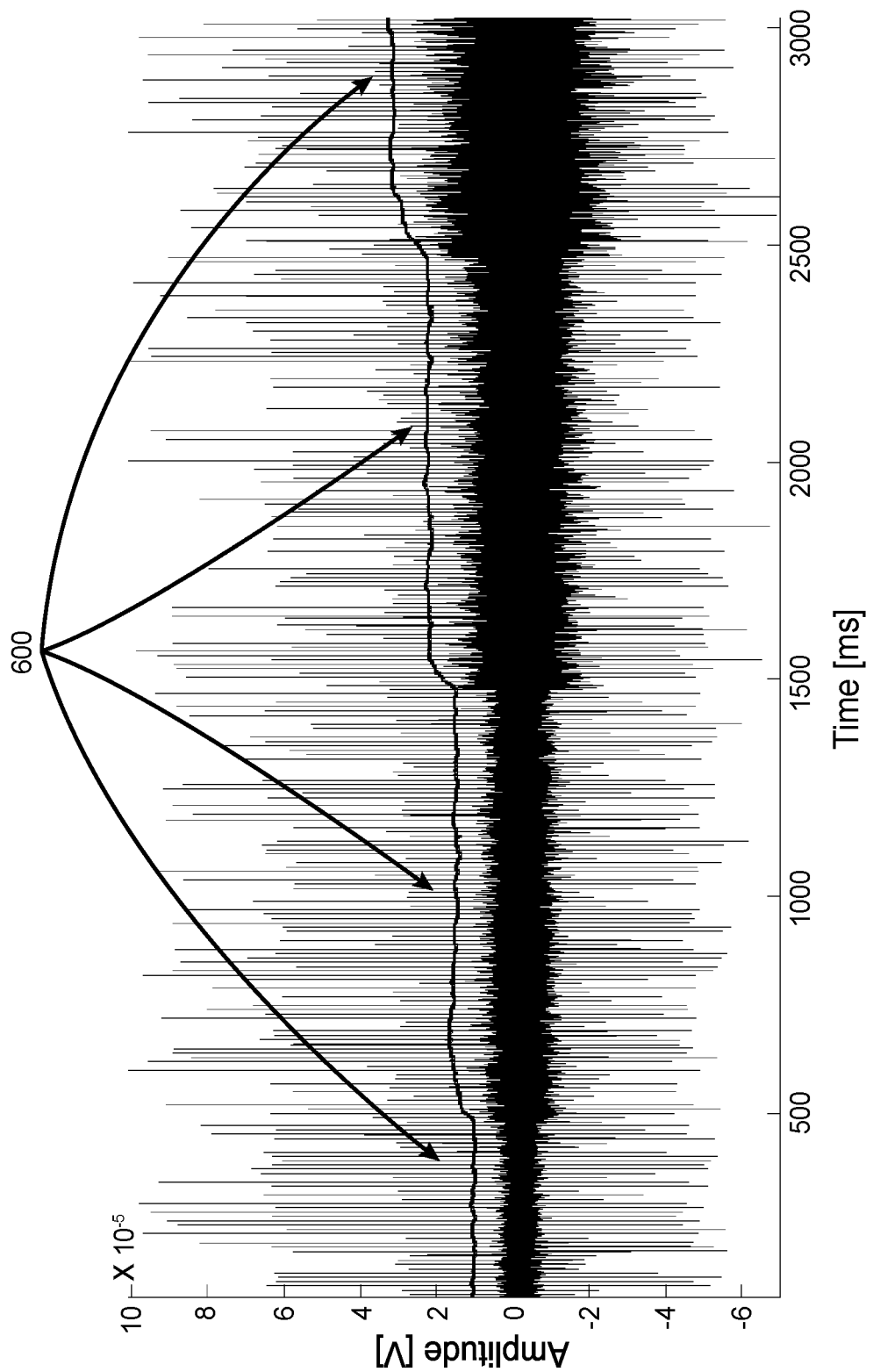
FIG. 6 is a graph illustrating variations in threshold estimations by an embodiment of a spike detection system in a test configuration where a signal-to-noise ratio (SNR) of a test signal decreases from 20 dB, 15 dB, 10 dB, to 5 dB with a firing rate of 100 spikes per second.

Table I of FIG. 8 shows the detection performances for a 20s input signals with different SNRs of 15 dB, 10 dB, 5 dB and 0 dB, and firing rates varying from 25 to 125 spikes/s. As it can be seen, the optimized SDCLT competes very well with other resources demanding methods. Furthermore, at 0 dB, the proposed method gets better true detection results than the RMS value. The only noticeable drawback come from a slightly increase in the false positive, which is not significant (only 5.87% at 0 dB). To get an insight on the threshold robustness to noise variations, FIG. 6 shows the threshold variations 600 in response to SNR variations in the channel going from 20 dB, 15 dB, 10 dB, to 5 dB with a constant 100 spikes/s firing rate. As expected, the threshold response is similar to the one of a first order system, which can be modified by changing the parameters described earlier.

Table II of FIG. 9 shows the execution time with an MCU clock frequency of 8 MHz for one channel of the proposed SDCLT method, for its counterpart with no optimization (using of floating numbers, divisions and multiplication), and for the RMS method optimized to use only multiplications and shifting operations (as described in the embodiments herein-above). It can be observed that the proposed SDCLT method reduces the calculation time tremendously. Furthermore, it was the only method capable of handling two recording channels (12.5 µs maximum per channels) on our optogenetic platform.

Table III of FIG. 10 shows the resource utilization of the proposed adaptive threshold algorithm (implemented in our testing platform) compared with the other methods (implemented in Matlab). As can be observed, the proposed algorithm does not rely on any multiplications or divisions unlike others, and is using less memory (only 32 bytes per channel). For instance, the RMS algorithm and the sliding-window MAD algorithm are using a sliding buffer of 1024 samples, leading to the utilization of 2048 bytes of memory per channel for 16 bits samples (same resolution as our testing platform), while the MAD1 operator necessitates a large buffer to store all samples. Furthermore, the RMS algorithm necessitates a square root operation, while the MAD operator necessitates many comparisons between all samples in order to find the median. Both the square root and the median cannot be calculated in a low-power embedded system, while, in contrast the proposed method is suited for such types of system since it uses only basic operations and low memory. Thus, the proposed method is better suited for embedded MCU or FPGA implementations than these other detectors because it has a lower memory and logic footprint (64 times less memory and do not require any complex operations). It should be noted that the threshold gain is assumed to be processed by a right bit shifting operation of 2 positions in all algorithms, and that the division-by-n in the RMS algorithm (n=1024) is calculated by shifting the bit 10 position to the left.

Figure 7:
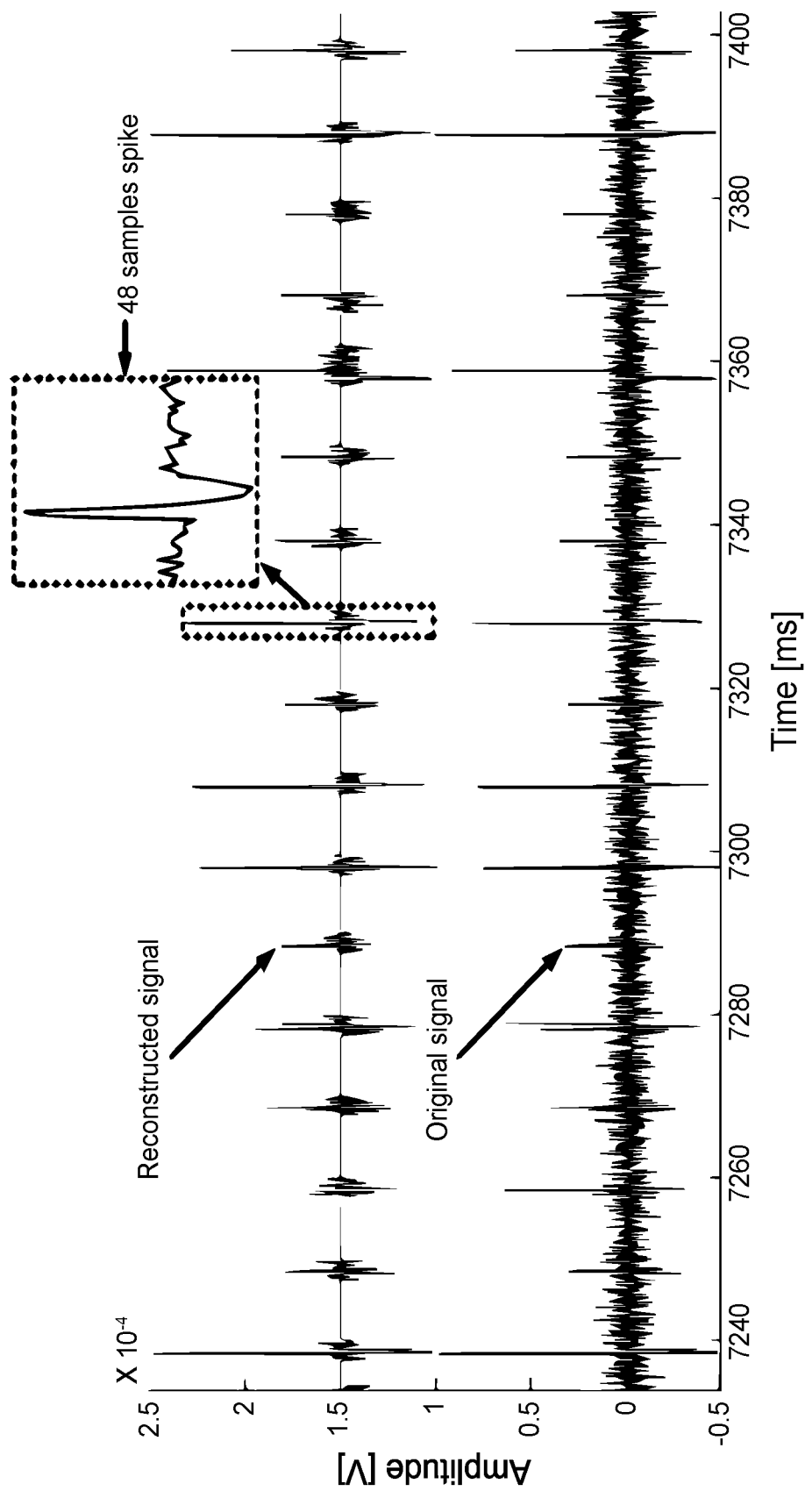
FIG. 7 illustrates an original signal next to an action potential (AP) signal reconstructed from spikes detected in the original signal using an embodiment of a spike detection system.

FIG. 7 shows the reconstructed signal, built using the detected and transmitted AP waveforms at their respective time stamp positions, versus the original signal. Except for the measured noise between the APs, the two waveforms that are employed to compare the proposed detector with other approaches are identical.

The invention claimed is:

1. A method for determining a threshold for spike detection in a noisy signal in real-time, the method comprising the steps of:
   a) receiving the noisy signal;
   b) measuring a current instantaneous value of the noisy signal;
   c) estimating a current variability of noise in the noisy signal according to the current instantaneous value and a window of previous instantaneous values using a sigma-delta control loop;
   d) determining the threshold based on the estimated variability of the noise; and
   e) repeating steps a) through d) to update the current estimate of the variability of the noise and adjust the threshold in real-time as the noisy signal changes.

2. The method according to claim 1, wherein the noisy signal is an electrophysiological signal.

3. The method according to claim 1, wherein estimating the variability of the noise comprises estimating a standard deviation of the noise, and wherein determining the threshold comprises scaling the estimated standard deviation by a predetermined factor.

4. The method according to claim 3, wherein estimating the standard deviation comprises:
   providing a target probability corresponding to a probability that the noise is greater than one standard deviation; and
   adjusting the estimated standard deviation such that a ratio of the current and previous instantaneous values greater than the estimated standard deviation corresponds to the target probability.

5. The method according to claim 4, wherein the target probability is approximately 31.7%.

6. The method according to claim 4, further comprising maintaining a counter corresponding to the ratio of the current and previous instantaneous values greater than the estimated standard deviation and, following each measurement of the instantaneous value, updating the counter and incrementally adjusting the estimated standard deviation according to an error between the counter and the target probability.

7. The method according to claim 6, further comprising maintaining a buffer of a predetermined length, the buffer comprising results of comparisons between the current and previous instantaneous values and the estimated standard deviation; and wherein upon measuring the current instantaneous value:
  if the instantaneous value is less than the estimated standard deviation and the oldest comparison in the buffer corresponds to an oldest value in the window being greater than or equal to the standard deviation, incrementing the counter; and
  if the instantaneous value is greater than or equal to the estimated standard deviation and the oldest comparison in the buffer corresponds to an oldest value in the window being less than the standard deviation, decrementing the counter.

8. The method according to claim 4, wherein upon measuring the current instantaneous value, performing the steps of: calculating an error between the target probability and the ratio of the current and previous instantaneous values greater than the estimated standard deviation, and incrementally adjusting the estimated standard deviation by adding thereto the error multiplied by a predetermined factor.

9. The method according to claim 8, wherein multiplication by the predetermined factor is approximated by a bit shifting operation.

10. The method according to claim 1, further comprising taking an absolute value of the current and previous instantaneous values, and wherein estimating the variability of the noise amplitude comprises modelling an amplitude of the noise according to a half-normal distribution.

11. The method according to claim 1, wherein estimating the current variability of the noise comprises:
  comparing the current instantaneous value with the current estimated variability, and maintaining comparison results for the window of previous instantaneous values;
  calculating a ratio of positive comparison results to negative comparison results;
  calculating an error between the ratio and a predetermined target probability; and
  adjusting the current estimate of the variability to reduce the error.

12. The method according to claim 1, further comprising detecting spikes in the electrophysiological signal by identifying instantaneous values of the electrophysiological signal above the determined threshold.

13. The method according to claim 12, further comprising operating a brain-machine interface (BMI) using the detected spikes, the detected spikes corresponding to action potential in the electrophysiological signal.

14. A non-transitory computer readable storage medium comprising instructions that cause a processing unit of a system for determining a threshold for spike detection in a noisy signal in real-time to:
  a) receive the noisy signal;
  b) measure a current instantaneous value of the noisy signal;
  c) estimate a current variability of noise in the noisy signal according to the current instantaneous value and a window of previous instantaneous values using a sigma-delta control loop;
  d) determine the threshold based on the estimated variability of the noise; and
  e) repeat steps a) through d) to update the current estimate of the variability of the noise and adjust the threshold in real-time as the noisy signal changes.

15. A low power digital system for determining a threshold for spike detection in a noisy signal in real-time, the system comprising:
  an input for receiving and sampling the electrophysiological signal;
  a comparator configured to receive a value of the sample and compare the value with a control signal corresponding to an estimate of a variability of noise in the signal, the comparator generating a pulse width modulated (PWM) signal with a duty cycle encoding results of the comparison;
  a demodulator operatively connected to the comparator, the demodulator being configured to demodulate the PWM signal and obtain a duty cycle thereof;
  an arithmetic module operatively connected to the demodulator, the arithmetic module being configured to generate an error signal corresponding to an error between the duty cycle and a target probability;
  an integrator operatively connected to the arithmetic module, the integrator being configured to generate the control signal and estimate the variability of the noise in the signal by reducing the error signal; and
  a gain module operatively connected to the regulator, the gain module being configured to receive the control signal and multiply it by a predetermined factor to obtain the threshold for spike detection.

16. The low power digital system according to claim 15, further comprising an absolute value operator configured to compute an amplitude of the sampled electrophysiological signal, said amplitude corresponding to the value of the sample.

17. The low power digital system according to claim 15, wherein the comparator is configured to generate a PWM signal with a duty cycle encoding a number of samples which are greater than an estimated standard deviation of the noise in the signal.

18. The low power digital system according to claim 15, wherein the demodulator is configured to demodulate the PWM signal over a window of previous comparison results.

19. The low power digital system according to claim 15, wherein the PWM signal is stored in a circular buffer of a fixed size, the buffer size corresponding to a size of the window of previous comparisons which are to be demodulated.

20. The low power digital system according to claim 19, wherein the buffer size is between 32 and 8192 bits.

21. The low power digital system according to claim 19, wherein each bit of the buffer corresponds to a binary result of the comparator following comparison of a given sample value with the control signal.

22. The low power digital system according to claim 21, wherein the demodulator comprises a counter configured to maintain a count of the binary comparison results in the circular buffer.

23. The low power digital system according to claim 22, wherein the arithmetic module is configured to subtract the count from the target probability multiplied by the buffer length, thereby generating the error signal corresponding to the error between the duty cycle and the target probability multiplied by the buffer length, and wherein the predetermined factor in the integrator accounts for the buffer length, thereby allowing for the error signal to be generated without a division operation.

24. The low power digital system according to claim 15, wherein the integrator is configured to obtain a current estimate of the variability of the noise by adding a previous estimate of the variability of the noise with the error signal multiplied by a predetermined factor.

25. The low power digital system according to claim 24, wherein the predetermined factor multiplying the error signal is approximated by applying a bit shifting operation to the error signal.

26. The low power digital system according to claim 15, wherein the comparator, demodulator and integrator are implemented exclusively using addition, comparison and multiplication operations.

27. The low power digital system according to claim 26, wherein at least some of the multiplication operations are approximated using bit shifting operations.

28. The low power digital system according to claim 15, wherein the target probability is approximately 31.7% and corresponds to a probability of noise being greater than one standard deviation in a half normal distribution.

29. The low power digital system according to claim 15, further comprising a spike detection module configured to detect spikes in the electrophysiological signal corresponding to samples having values greater than the determined threshold.

30. The low power digital system according to claim 15, wherein an output of the spike detection module is operatively connected to a computing unit, the detected spikes serving as an input to operate the computing unit as part of a brain-machine interface (BMI).

31. The low power digital system according to claim 15, wherein the noisy signal is an electrophysiological signal, and wherein the input comprises an electrode for interfacing with biological tissue and acquiring the electrophysiological signal therefrom.

* * * * *